United States Patent
Clark et al.

(10) Patent No.: US 7,011,213 B2
(45) Date of Patent: Mar. 14, 2006

(54) PROTECTIVE SHIELD FOR A PATIENT CONTROL DEVICE

(75) Inventors: Dan Warren Clark, Amarillo, TX (US); Russell Dean Parker, Amarillo, TX (US)

(73) Assignee: Biotronics, Amarillo, TX (US)

( * ) Notice: Subject to any disclaimer, the term of this patent is extended or adjusted under 35 U.S.C. 154(b) by 0 days.

(21) Appl. No.: 10/752,600

(22) Filed: Jan. 7, 2004

(65) Prior Publication Data
US 2004/0140028 A1 Jul. 22, 2004

Related U.S. Application Data

(63) Continuation-in-part of application No. 10/214,518, filed on Aug. 8, 2002, now abandoned.

(60) Provisional application No. 60/390,619, filed on Jun. 21, 2002.

(51) Int. Cl.
*A61B 17/06* (2006.01)
(52) U.S. Cl. ........................................ 206/438; 206/305
(58) Field of Classification Search ............... 206/438, 206/320, 305, 570, 210, 439, 524.8, 363; 600/101, 102, 121, 122, 133; 224/222; 150/165; D6/449, 610, 567, 459, 466, 475; D14/250; 383/70, 74
See application file for complete search history.

(56) References Cited

U.S. PATENT DOCUMENTS

| | | | |
|---|---|---|---|
| 1,535,312 A * | 4/1925 | Hosking | 352/242 |
| 1,535,732 A * | 4/1925 | Malm | 383/71 |
| 4,008,851 A * | 2/1977 | Hirsch | 383/62 |
| 4,757,381 A * | 7/1988 | Cooper et al. | 348/66 |
| 4,819,846 A * | 4/1989 | Hannemann | 224/240 |
| 4,836,256 A | 6/1989 | Meliconi | |
| 4,957,231 A * | 9/1990 | Kalisher | 224/583 |
| 5,044,775 A * | 9/1991 | Rutledge | 383/72 |
| 5,092,459 A * | 3/1992 | Uljanic et al. | 206/320 |
| 5,214,794 A | 5/1993 | Van Wijnen | |
| 5,286,110 A * | 2/1994 | Benson et al. | 383/5 |
| 5,316,141 A | 5/1994 | Jalomo | |
| 5,383,091 A | 1/1995 | Snell | |
| D355,791 S * | 2/1995 | Briley | D6/449 |
| 5,388,691 A | 2/1995 | White | |
| D361,912 S * | 9/1995 | Cleland | D6/449 |
| D369,607 S * | 5/1996 | MacGilvary et al. | D14/250 |
| D372,145 S * | 7/1996 | Elmer | D6/475 |
| 5,539,162 A * | 7/1996 | Tuttle | 181/131 |
| 5,592,946 A * | 1/1997 | Eddy | 600/528 |
| D378,020 S * | 2/1997 | Hatt | D3/218 |
| 5,694,299 A | 12/1997 | Mori | |
| 5,711,469 A * | 1/1998 | Gormley et al. | 224/675 |
| 5,733,023 A * | 3/1998 | Lee | 312/208.3 |
| 5,779,033 A * | 7/1998 | Roegner | 206/6.1 |
| 5,848,152 A | 12/1998 | Slipy | |
| 5,887,708 A * | 3/1999 | Gonzales | 206/209 |
| 5,923,752 A | 7/1999 | McBride | |
| 5,982,881 A | 11/1999 | Mischenko | |

(Continued)

*Primary Examiner*—Shian T. Luong
(74) *Attorney, Agent, or Firm*—Carlson, Gaskey & Olds

(57) ABSTRACT

A disposable shield designed to sheath a patient control device prevents contaminants from contacting or entering the device. The shield has a bi-directional opening through which the hand-operated device is inserted and removed from the shield. A removable sealing device is used to preserve the integrity of the shield when the sealing device is removed. The shield can therefore be changed each time the device is handled by a different person, minimizing the chances of cross-contamination. The shield also extends the life of the device by preventing biological contaminants from contacting the device.

12 Claims, 2 Drawing Sheets

U.S. PATENT DOCUMENTS

| | | | |
|---|---|---|---|
| D418,119 S * | 12/1999 | Rowell | D3/218 |
| D425,075 S * | 5/2000 | Perry | D14/250 |
| 6,064,735 A | 5/2000 | Wilkes | |
| 6,082,530 A * | 7/2000 | Wang-Chen | 206/45.24 |
| 6,082,535 A * | 7/2000 | Mitchell | 206/320 |
| 6,119,864 A * | 9/2000 | Kessler et al. | 206/704 |
| 6,132,367 A * | 10/2000 | Adair | 600/101 |
| 6,186,957 B1 * | 2/2001 | Milam | 600/528 |
| 6,201,867 B1 | 3/2001 | Koike | |
| D451,013 S * | 11/2001 | Bridwell et al. | D1/102 |
| D451,094 S * | 11/2001 | Powell | D14/250 |
| D459,346 S * | 6/2002 | Powell | D14/250 |
| 6,575,917 B1 * | 6/2003 | Giroux et al. | 600/528 |
| 6,659,274 B1 * | 12/2003 | Enners | 206/305 |
| 6,662,985 B1 * | 12/2003 | Harada et al. | 224/661 |

\* cited by examiner

PROTECTIVE SHIELD FOR A PATIENT CONTROL DEVICE

REFERENCE TO RELATED APPLICATIONS

This application is a continuation-in-part of U.S. application Ser. No. 10/214,518, filed on Aug. 8, 2002 now abandoned, which claims priority to U.S. Provisional Application No. 60/390,619 filed on Jun. 21, 2002.

TECHNICAL FIELD

The present invention relates to patient control devices, such as nursecalls, light controls, and television controls, used in medical facilities, and more particularly to a cover for protecting a patient control device.

BACKGROUND OF THE INVENTION

Medical facilities, such as hospitals, use patient control devices, such as nursecall devices, to allow patients to alert nurses and control environmental settings such as light levels and television channels. The nursecall device normally includes control circuitry inside a case and is placed in a patient's bed for easy access. Because the nursecall device can be located anywhere in the bed with the patient, the unit can easily become contaminated with various contaminants (e.g., debris, bodily excretions, bathwater, drugs, infectious bacteria and viruses, etc.). The case is cleaned and sterilized between patients, but this does not prevent contaminants from entering the nursecall device during use. These contaminants can damage the control circuitry, requiring the unit to be serviced. The nursecall device often also has buttons, switches, dials, and/or seams that may trap contaminants, making them difficult to remove. Further, contaminants can potentially leak back out of the unit, increasing the possibility of cross-contamination and/or cross-infections. In many cases, these contaminants are not detected until the nursecall device is taken apart for servicing.

Also, the case is often made of a porous material, making it susceptible to premature damage as it absorbs cleaning solvents and other liquids. The case should be cleaned frequently for proper hygiene, but the harsh solvents may discolor or even damage the case, especially over time.

There is a desire for a structure that prevents contaminants from entering the nursecall device or being trapped in crevices on the case while still allowing the nursecall device to be easily operable by a patient.

SUMMARY OF THE INVENTION

The present invention is directed to a shield that covers a patient control device, such as a nursecall device. In one embodiment, the shield is designed to form-fit the case of the nursecall device. Bubbles or soft elevations may be formed in the shield over buttons and/or dials on the nursecall device so they can be operated through the shield. The shield may be formed of a flexible, resilient light-passing material so that it fits snugly around the case to prevent contaminants from contacting or entering the nursecall device itself. By preventing contaminants from entering the nursecall device and damaging the nursecall device circuitry, the shield extends the life of the nursecall device and reduces the need for frequent servicing.

In one embodiment, the shield is a single-use, disposable shield having a bi-directional opening configuration that allows easy insertion and removal of the nursecall device. The shield can therefore be changed frequently and disposed, minimizing the chances of biological cross-contamination between patients.

DETAILED DESCRIPTION OF THE EMBODIMENTS

Figure 1:
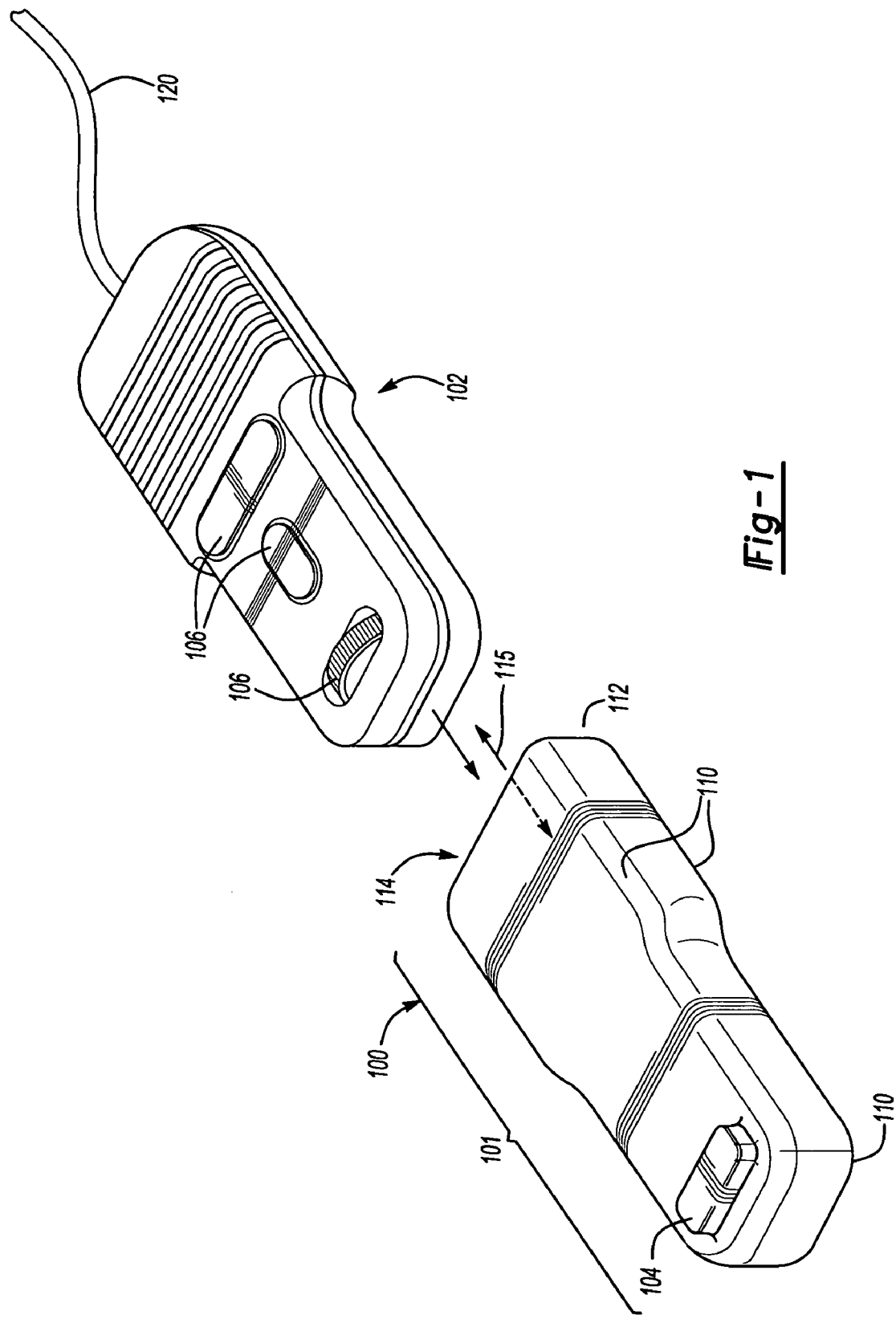
FIG. 1 is a perspective view of a shield according to one embodiment of the invention.
Figure 2:
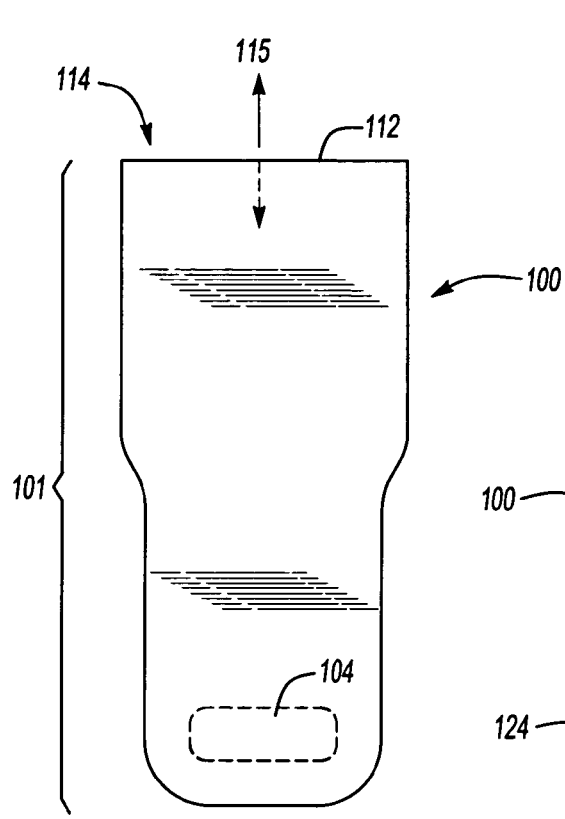
FIG. 2 is a plan view of one embodiment of the shield.

FIGS. 1 through 4 illustrate a shield 100 designed to cover a patient control device (e.g., a nursecall, television control, light control, all-in-one unit, etc) 102. In one embodiment, the shield 100 has a sheath portion 101 with a shape that generally matches the shape of the nursecall device 102 so that the shield 100 will conform to the nursecall device's 102 shape without leaving any undesired gaps between the shield 100 and the unit 102. In one embodiment, the sheath portion 101 has one or more elevations 104 that ultimately are aligned above one or more controls 106 on the nursecall device, such as a lever or a dial.

The material used to form the shield 100 may be any material that allows the sheath portion 101 to fit snugly around the nursecall device 102 while still being flexible enough to allow controls 106 to be operated through the elevations 104 and through the shield 100 itself. Because the controls 106 are touched frequently and often have crevices, they are normally prone to trapping biological contaminants. The elevations 104 guard the controls 106 by preventing direct contact between the controls 106 and any potential contaminants. Further, the elevations 104 allow tactile detection of the controls 106, while the flexibility of the shield material allows the user to push down on the elevation 104 to reach the controls 106. Note that elevations 104 do not need to be provided for every control 106 on the unit 102. As shown in FIG. 1, for example, the controls 106 also include buttons that can be operated directly through the sheath portion 101 of the shield 100. Generally, an elevation 104 may be included for any control 104, such as a dial or a lever, whose operation may involve more freedom of movement than an unelevated sheath 101 area would allow.

In one embodiment, the shield 100 material is also resilient so that it can be stretched around the nursecall device 102 as the nursecall device 102 is inserted into the sheath portion 101 while still being able to conform itself around the nursecall device 102. Possible shield materials include, but are not limited to, polyurethane, vinyl, latex, nitrile, or any other materials having similar resilient properties. In one embodiment, the shield 100 is made of a synthetic material.

The shield 100 may be formed via any known manufacturing process that is appropriate for the material being used, including but not limited to casting, blow molding, and dip casting. The material itself may be woven or a film, depending on the desired characteristics of the shield 100. Those of ordinary skill in the art will recognize that other materials and other manufacturing processes can be used to form the shield 100 without departing from the scope of the invention. In one embodiment, the shield 100 material is between 1 and 5 mm thick and passes light so that the controls 106 and/or labels on the nursecall device 102 can be seen through the sheath portion 101. Further, the shield 100 is preferably seamless, with no cracks or crevices that could trap contaminants. The shield 100 may be formed with rounded edges 110 to simplify manufacturing and to improve the appearance of the shield 100 when it is on the nursecall device 102. The shield 100 may also be designed to allow clearance between the shield 100 and the nursecall device 102 to make the shield 100 easier to install and remove.

The shield 100 has an open edge 114 of a bi-directional passage 115 through which the device 102 is inserted and removed. Although the illustrated embodiment shows an open edge 114 having the same width as the widest portion of the nursecall device 102, the material used for the shield 100 may be resilient enough to allow the open edge 114 to be narrower than the nursecall device 102. This would allow at least a portion of the top of the nursecall device 102 to be covered by the shield 100.

Figure 3:
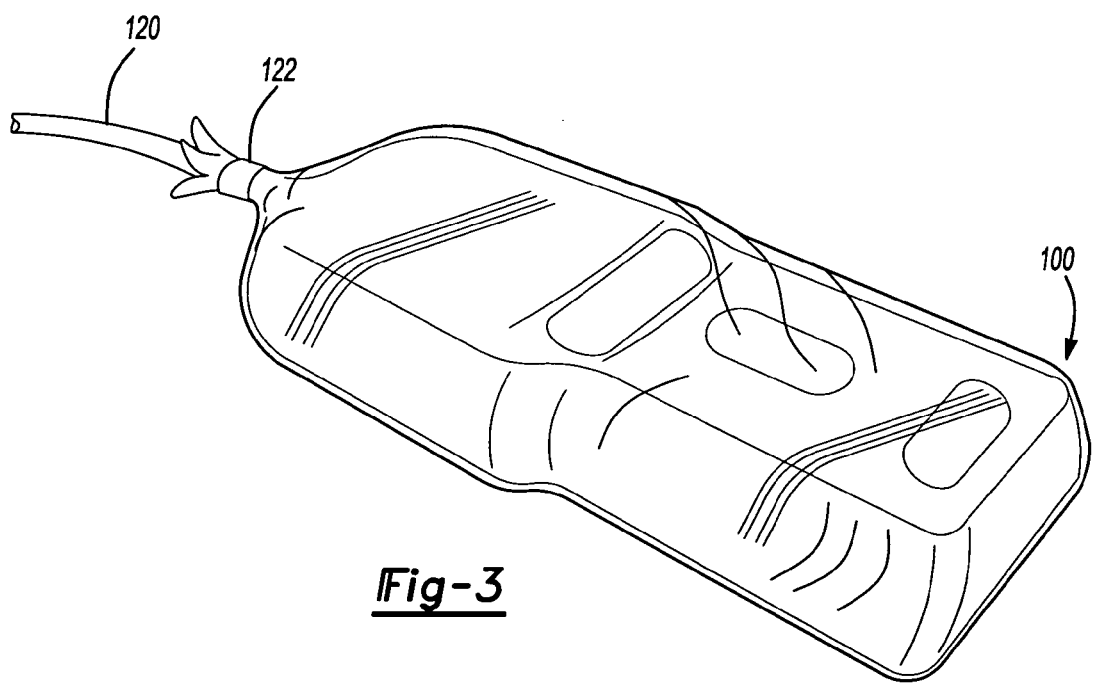
FIG. 3 is a perspective view of the shield attached to a nursecall unit.

As shown in FIG. 3, the open edge 114 of the shield 100 may be bunched around a cord 120 of the nursecall device 102 and sealed by a clamp, adhesive tape, or other removable sealing device 122 attached to the cord 120. Regardless of the specific sealing device 122 used, it should be removable without damaging the shield 100 to maintain the integrity of the bi-directional passage 115. This ensures that the shield 100 can be removed from the shield 100 through the same passage 115 that it was inserted. By using a removable sealing device 122, the shield 100 can be removed cleanly without cutting or rupturing the shield 100, which would otherwise cause biological contaminants on the shield surface to contact the nursecall device 102.

Figure 4:
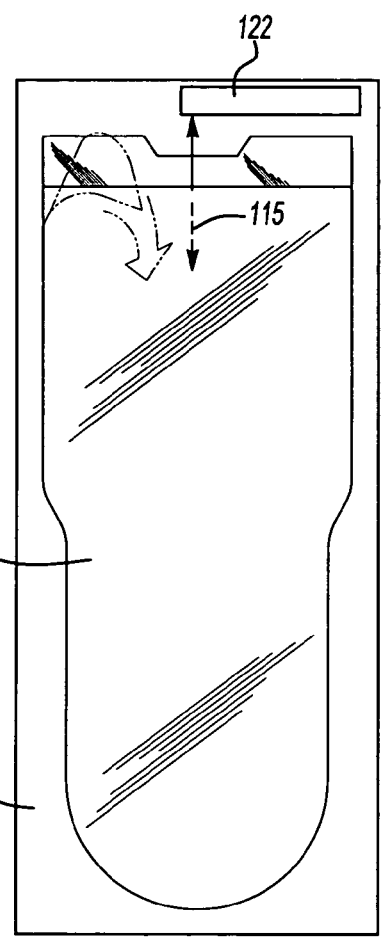
FIG. 4 is a plan view of another embodiment of the shield.

FIG. 4 is a plan view of the shield 100 attached to a backing 124, such as a paper backing. The backing 124 stabilizes the shield 100 so that the nursecall device 102 can be inserted easily into the shield 100. Once the nursecall device is inserted into the shield 100, the backing 124 can be peeled off to free the shield 100 and allow the sealing device 122 to be attached. In one embodiment, the sealing device 122 is an adhesive strip that can also be peeled off the backing 124 and wrapped around the cord 120. By placing both the shield 100 and the sealing device 122 on the same backing, the invention is more convenient to use.

As a result, the inventive shield structure blocks contaminants from being trapped on or inside a patient nursecall device, reducing the risks of cross-contamination when the units are handled by multiple people. The shield also protects the nursecall device itself by blocking contaminants from entering the nursecall device and damaging the circuitry and preventing harsh fluids, such as cleaning solvents, from damaging the exterior case of the nursecall device. Because the shield is disposable, it can be frequently changed as needed to keep the nursecall device clean. Also, the dimensions of the shield can be customized so that it can precisely fit any particular nursecall device or other patient control device; different shields can be used for different devices.

Although a preferred embodiment of this invention has been disclosed, a worker of ordinary skill in the art would recognize that certain modifications would come within the scope of this invention. For that reason, the following claims should be studied to determine the true scope and content of this invention.

What is claimed is:

1. A sanitary hand-held nursecall device comprising:
   a shield including:
   a sheath portion having a sheath shape that substantially conforms to a device shape of the hand-held nursecall device, wherein the sheath portion is made of a flexible, resilient material that blocks biological contaminants from reaching the hand-held nursecall device;
   a bi-directional passage having an open edge that facilitates insertion and removal of the hand-held nursecall device into the sheath portion; and
   a removable sealing device that closes the bi-directional passage after the hand-held nursecall device has been inserted into the sheath portion;
   a hand-held nursecall device disposed within the shield; and
   a backing, wherein the shield is removably disposed on the backing and the removable sealing device is also removably disposed on the backing.

2. The sanitary hand-held nursecall device of claim 1, wherein the flexible material is a synthetic material.

3. The sanitary hand-held nursecall device of claim 2, wherein the synthetic material is one selected from the group consisting of polyurethane, vinyl, latex, and nitrile.

4. The sanitary hand-held nursecall device of claim 1, wherein the flexible material is one selected from a woven material and a film material.

5. The sanitary hand-held nursecall device of claim 1, wherein the flexible material is a light-passing material.

6. The sanitary hand-held nursecall device of claim 1, further comprising an elevation, wherein the elevation is disposed over a control on the hand-held patient control device when the hand-held patient control device is inserted into the sheath portion.

7. The sanitary hand-held nursecall device of claim 1, wherein the removable sealing device is one selected from the group consisting of an adhesive strip and a clamp.

8. The sanitary hand-held nursecall device of claim 1, wherein the hand-held nursecall device includes a cord portion and the removable sealing device is disposed around the cord portion to close the bi-directional passage around the cord portion, wherein the removable sealing device is one selected from the group consisting of an adhesive strip and a clamp.

9. A shield for a hand-operated patient control device, the shield comprising:
   a sheath portion having a sheath shape that substantially conforms to a device shape of the hand-operated patient control device, wherein the sheath portion is made of a flexible, resilient material that blocks biological contaminants from reaching the hand-held patient control device;
   a bi-directional passage having an open edge that facilitates insertion and removal of the hand-operated patient control device into the sheath portion;
   a removable sealing device that closes the bi-directional passage after the hand-operated patient control device has been inserted into the sheath portion; and
   a backing, wherein the shield is removably disposed on the backing, and wherein the removable sealing device is also removably disposed on the backing.

10. A shield for a hand-held nursecall device having at least one control, the shield comprising:
    a sheath portion having a sheath shape that substantially conforms to a device shape of the hand-held nursecall device;
    at least one elevation formed in the sheath portion, wherein the at least one elevation is disposed over the at least one control when the hand-held nursecall device is inserted into the shield;

a bi-directional passage having an open edge that facilitates insertion and removal of the hand-held nursecall device into the sheath portion;

a removable sealing device that closes the bi-directional passage after the hand-held nursecall device has been inserted into the sheath portion, wherein the removable sealing device is disposed around a cord connected to the hand-held nursecall device; and a backing supporting the shield, wherein the removable sealing device is also removably disposed on the backing, wherein the shield is made of a flexible, resilient, light-passing material that blocks biological contaminants from reaching the hand-held nursecall device and is removable from the backing.

11. The shield of claim 10, wherein the flexible, resilient, light-passing material is one selected from the group consisting or polyurethane, vinyl, latex, and nitrile.

12. The shield of claim 10, wherein the removable sealing device is one selected from the group consisting of an adhesive strip and a clamp.

* * * * *